US012780821B2

(12) United States Patent
Kysil et al.

(10) Patent No.: US 12,780,821 B2
(45) Date of Patent: *Nov. 3, 2026

(54) COMPOUNDS HAVING ((3-NITROPHENYL)SULFONYL)ACETAMIDE AS BCL-2 INHIBITORS

(71) Applicant: Eil Therapeutics, Inc., San Diego, CA (US)

(72) Inventors: Volodymyr Kysil, San Diego, CA (US); Vladislav Zenonovich Parchinsky, Moscow (RU); Alexei Pushechnikov, San Diego, CA (US); Alexandre Vasilievich Ivachtchenko, Hallandale Beach, FL (US); Ruben Abagyan, La Jolla, CA (US); Andrew Orry, San Diego, CA (US); Polo Chun-Hung Lam, San Diego, CA (US); Nikolay Savchuk, San Diego, CA (US)

(73) Assignee: Eil Therapeutics, Inc., Dover, DE (US)

( * ) Notice: Subject to any disclaimer, the term of this patent is extended or adjusted under 35 U.S.C. 154(b) by 614 days.

This patent is subject to a terminal disclaimer.

(21) Appl. No.: 18/222,370

(22) Filed: Jul. 14, 2023

(65) Prior Publication Data

US 2023/0357238 A1 Nov. 9, 2023

Related U.S. Application Data

(63) Continuation-in-part of application No. 17/698,956, filed on Mar. 18, 2022, now Pat. No. 11,834,450.

(60) Provisional application No. 63/163,326, filed on Mar. 19, 2021.

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
See application file for complete search history.

(56) References Cited

U.S. PATENT DOCUMENTS 8,563,735 B2 * 10/2013 Bruncko ................. A61P 25/00
546/300
11,834,450 B2 * 12/2023 Kysil ..................... A61K 45/06

* cited by examiner

*Primary Examiner* — Jeffrey S Lundgren
*Assistant Examiner* — Eric Tran
(74) *Attorney, Agent, or Firm* — Sergey Alyabyev

(57) ABSTRACT

The present invention is generally directed to inhibitors of BCL-2 proteins useful in the treatment of diseases and disorders modulated by BCL-2 and having the Formula (A):

(A)

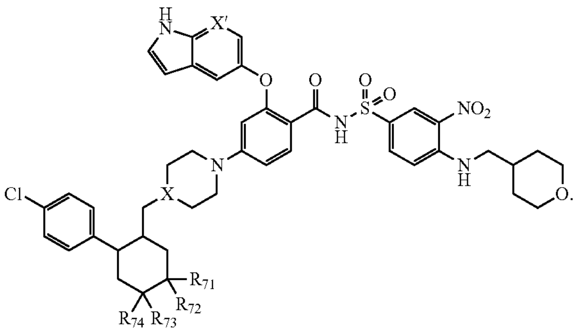

13 Claims, No Drawings

COMPOUNDS HAVING ((3-NITROPHENYL)SULFONYL)ACETAMIDE AS BCL-2 INHIBITORS

CROSS-REFERENCE TO RELATED INVENTIONS

This application is a Continuation-In-Part under 35 USC § 120 of U.S. application Ser. No. 17/698,956 filed Mar. 18, 2022 and entitled "Compounds Having ((3-Nitrophenyl) sulfonylacetamide as BCL-2 Inhibitors," which claims priority to, and the benefit of, U.S. Provisional Application Ser. No. 63/163,326 filed Mar. 19, 2021 and entitled "Compounds Having ((3-Nitrophenyl)sulfonylacetamide as BCL-2 Inhibitors," the entire contents of both of which applications are incorporated by reference herein, for all purposes.

FIELD OF INVENTION

The present invention is directed to inhibitors of B-cell lymphoma 2 (BCL-2) proteins. The inhibitors described herein can be useful in the treatment of diseases or disorders associated with BCL-2. In particular, the invention is concerned with compounds and pharmaceutical compositions inhibiting BCL-2, methods of treating diseases or disorders associated with BCL-2, and methods of synthesizing these compounds.

BACKGROUND OF THE INVENTION

Apoptosis, or programmed cell death, is a physiological process that is crucial for embryonic development and maintenance of tissue homeostasis.

Deregulation of apoptosis is involved in certain pathologies. Increased apoptosis is associated with neurodegenerative diseases such as Parkinson's diseases Alzheimer's disease and ischaemia. Conversely, deficits in the implementation of apoptosis play a significant role in the development of cancers and their chemoresistance, in autoimmune diseases, inflammatory diseases and viral infections. Accordingly, absence of apoptosis is one of the phenotypic signatures of cancer (Hanahan, D. et al., Cell, 2000, 100, 57-70).

The BCL-2 family of proteins plays a major role in tumorogenesis. BCL-2 proteins are characterized based on the presence of BCL-2 homology (BH) domains. The anti-apoptotic proteins contain all the BH1-4 domains; the pro-apoptotic proteins contain either the BH3 domain only or multiple domains. The BH3 domain is necessary in executing the pro apoptotic function of these proteins. In anti-apoptotic proteins, the BH3 domain remains hidden or buried inside other BH domains and hence they exclusively function as protectors of cell survival. The BCL-2 proteins use BH domains to interact with each other. The anti-apoptotic BCL-2 proteins interact with pro-apoptotic members and inhibit their function to maintain cellular homeostasis. It is the shift in balance between anti-apoptotic and pro-apoptotic BCL-2 proteins that may decide the fate of cancer cells.

Cancer therapeutics targeting the BCL-2 family mainly have focused on neutralizing one or more anti-apoptotic members by inhibiting their function using small molecule inhibitors or by suppressing their expression utilizing antisense oligonucleotides. The concept was to inhibit the anti-apoptotic BCL-2 members' function and thus allowing pro-apoptotic members to induce cell death in cancer cells. However, cancer cells treated with BCL-2 inhibitors were found to upregulate other anti-apoptotic BCL-2 or non-BCL-2 family proteins involved in cell survival, resulting in therapeutic resistance.

There is a need for therapeutic agents that can induce cell death in tumors or cancers with increased expression of BCL-2. This invention is intended to fill this unmet needs associated with current BCL-2 inhibition therapy.

SUMMARY OF THE INVENTION

A first aspect of the invention relates to compounds of Formula (A):

(A)

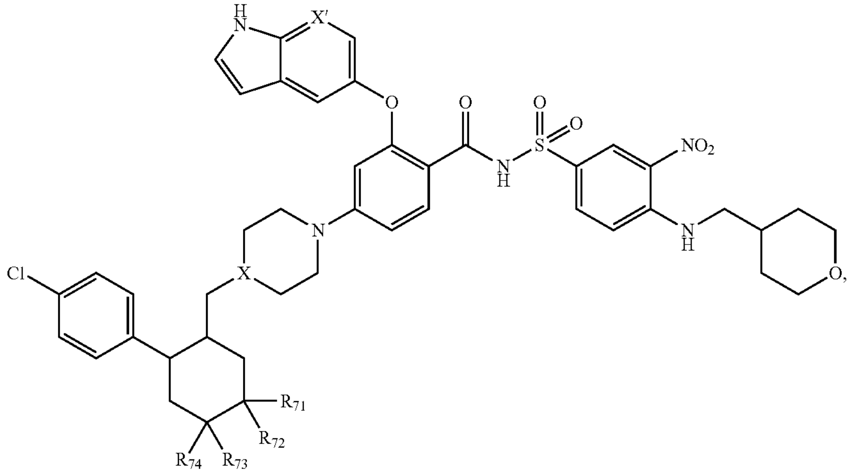

and pharmaceutically acceptable salts, isomers, solvates, prodrugs, or tautomers thereof, wherein:

X is selected from N and CH;

X' is selected from N and CH;

$R_{71}$ is selected from H, $C_1$-$C_6$ alkyl;

$R_{72}$ is selected from H and OH;

$R_{73}$ is selected from H and OH;

provided that at least one from $R_{72}$ and $R_{73}$ is OH or $R_{72}$ and $R_{73}$ together form a bond;

$R_{74}$ is selected from H, $C_1$-$C_6$ alkyl.

Another aspect of the invention is directed to pharmaceutical compositions comprising a compound of Formula (A), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the invention relates to a method of treating a disease or disorder associated with modulation of BCL-2 proteins, such as Isoform 1 and Isoform 2. The method comprises administering to a patient in need of a treatment for diseases or disorders associated with modulation of BCL-2 proteins an effective amount of a compound of Formula (A), or a pharmaceutically acceptable salt, hydrate, solvate, prodrug, stereoisomer, tautomer, or pharmaceutical composition thereof.

Another aspect of the invention is directed to a method of inhibiting BCL-2 proteins including, but not limited to Isoform 1 and Isoform 2. The method involves administering to a patient in need thereof an effective amount of a compound of Formula (A), or a pharmaceutically acceptable salt, hydrate, solvate, prodrug, stereoisomer, tautomer, or pharmaceutical composition thereof.

Another aspect of the invention is directed to a method of treating or preventing a disease or disorder disclosed herein in a subject in need thereof. The method involves administering to a patient in need thereof an effective amount of a compound of Formula (A), or a pharmaceutically acceptable salt, hydrate, solvate, prodrug, stereoisomer, tautomer, or pharmaceutical composition thereof.

Another aspect of the present invention relates to compounds of Formula (A), and pharmaceutically acceptable salts, hydrates, solvates, prodrugs, stereoisomers, tautomers, or pharmaceutical compositions thereof, for use in the manufacture of a medicament for inhibiting BCL-2 proteins, such as Isoform 1 and Isoform 2.

Another aspect of the present invention relates to compounds of Formula (A), and pharmaceutically acceptable salts, hydrates, solvates, prodrugs, stereoisomers, tautomers, or pharmaceutical compositions thereof, for use in the manufacture of a medicament for treating or preventing a disease or disorder disclosed herein.

Another aspect of the present invention relates to the use of a compound of Formula (A), or a pharmaceutically acceptable salt, hydrate, solvate, prodrug, stereoisomer, tautomer, or pharmaceutical composition thereof, in the treatment of a disease associated with inhibiting BCL-2 proteins, such as Isoform 1 and Isoform 2.

Another aspect of the present invention relates to the use of a compound of Formula (A), or a pharmaceutically acceptable salt, hydrate, solvate, prodrug, stereoisomer, tautomer, or pharmaceutical composition thereof, in the treatment of a disease or disorder disclosed herein.

The present invention further provides methods of treating a disease or disorder associated with modulation of BCL-2 proteins including, cancer and metastasis, comprising administering to a patient suffering from at least one of said diseases or disorders a compound of Formula (A), or a pharmaceutically acceptable salt, hydrate, solvate, prodrug, stereoisomer, tautomer, or pharmaceutical composition thereof.

The present invention provides inhibitors of BCL-2 proteins that are therapeutic agents in the treatment of diseases such as cancer and metastasis.

The present invention further provides compounds and compositions with an improved efficacy and safety profile relative to known BCL-2 protein inhibitors. The present disclosure also provides agents with novel mechanisms of action toward BCL-2 protein in the treatment of various types of diseases including cancer and metastasis.

In some aspects, the present disclosure provides a compound obtainable by, or obtained by, a method for preparing compounds described herein (e.g., a method comprising one or more steps described in General Schemes A-F).

In some aspects, the present disclosure provides an intermediate as described herein, being suitable for use in a method for preparing a compound as described herein (e.g., the intermediate is selected from the intermediates described in Examples).

In some aspects, the present disclosure provides a method of preparing a compound of the present disclosure.

In some aspects, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims

DETAILED DESCRIPTION OF THE INVENTION

The present disclosure relates to compounds and compositions that are capable of inhibiting the activity BCL-2 proteins including, but not limited to Isoform 1 and Isoform 2. The disclosure features methods of treating, preventing or ameliorating a disease or disorder in which BCL-2 plays a role by administering to a patient in need thereof a therapeutically effective amount of a compound of Formula (A), or a pharmaceutically acceptable salt, hydrate, solvate, prodrug, stereoisomer, or tautomer thereof. The methods of the present invention can be used in the treatment of a variety of BCL-2 mediated diseases and disorders by inhibiting the activity of BCL-2 proteins. Inhibition of BCL-2 can be an effective approach to the treatment, prevention, or amelioration of diseases including, but not limited to, cancer and metastasis. Decreasing BCL-2 activity can suppress cancer mutagenesis, dampen tumor evolution, and/or decrease the probability of adverse outcomes, such as drug resistance and/or metastases.

In a first aspect of the invention, the compounds of Formula (I) are described:

(A)

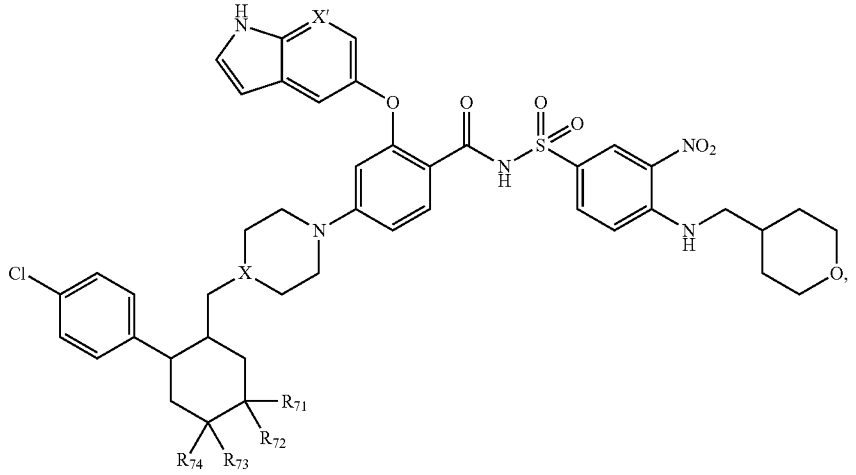

and pharmaceutically acceptable salts, hydrates, solvates, prodrugs, stereoisomers, and tautomers thereof, wherein X, X', $R^{71}$, $R^{72}$, $R^{73}$, and $R^{74}$ n are described herein.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DEFINITIONS

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

"Alkyl" refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The present invention also contemplates isotopically-labelled compounds of Formula I (e.g., those labeled with $^2H$ and $^{14}C$). Deuterated (i.e., $^2H$ or D) and carbon-14 (i.e., $^{14}C$) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labelled reagent for a non-isotopically labelled reagent.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease or disorder in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting BCL-2 proteins, such as Isoform 1 and Isoform 2, which are useful for the treatment of diseases and disorders associated with modulation of an BCL-2 protein. The invention further relates to compounds, or pharmaceutically acceptable salts, hydrates, solvates, prodrugs, stereoisomers, or tautomers thereof, which can be useful for inhibiting BCL-2.

In some embodiments, the compounds of Formula (A) have the structure of Formula (A-I):

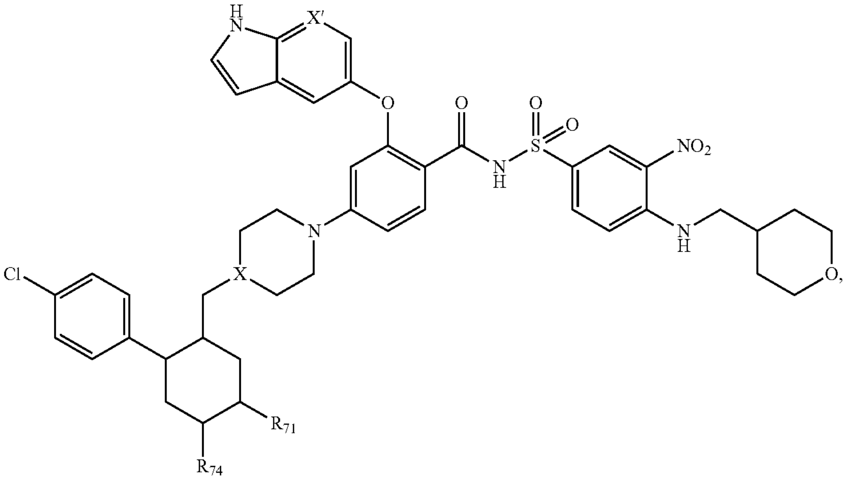

(A-I)

and pharmaceutically acceptable salts, isomers, solvates, prodrugs, or tautomers thereof, wherein X is selected from N and CH;

X' is selected from N and CH;

$R_{71}$ is selected from H, $C_1$-$C_6$ alkyl;

$R_{74}$ is selected from H, $C_1$-$C_6$ alkyl.

In some embodiments, X is N. In some embodiments, X is CH.

In some embodiments, X is N.

In some embodiments, X is CH.

In some embodiments, X' is N. In some embodiments, X' is CH.

In some embodiments, X' is N.

In some embodiments, X' is CH.

In some embodiments, $R_{71}$ is H. In some embodiments $R_{71}$ is $C_1$-$C_6$ alkyl.

In some embodiments, $R_{71}$ is H.

In some embodiments, $R_{71}$ is methyl.

In some embodiments, $R_{72}$ is H. In some embodiments, $R_{72}$ is OH.

In some embodiments, $R_{73}$ is H. In some embodiments, $R_{73}$ is OH.

In some embodiments, $R_{72}$ and $R_{73}$ together form a bond.

In some embodiments, $R_{74}$ is H. In some embodiments $R_{74}$ is $C_1$-$C_6$ alkyl.

In some embodiments, $R_{74}$ is H.

In some embodiments, $R_{74}$ is methyl.

Non-limiting illustrative compounds of the present disclosure include:

| Compound No | Structure | Name |
|---|---|---|
| 28 | 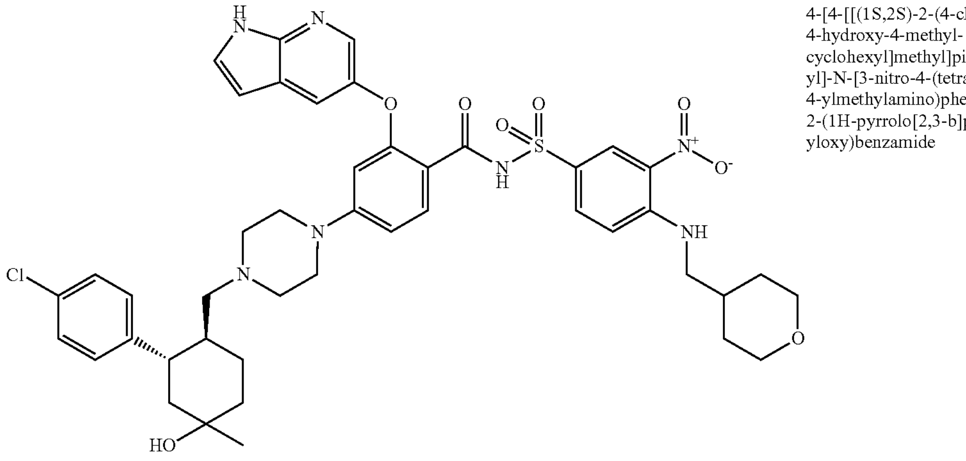 | 4-[4-[[(1S,2S)-2-(4-chlorophenyl)-4-hydroxy-4-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 29 | 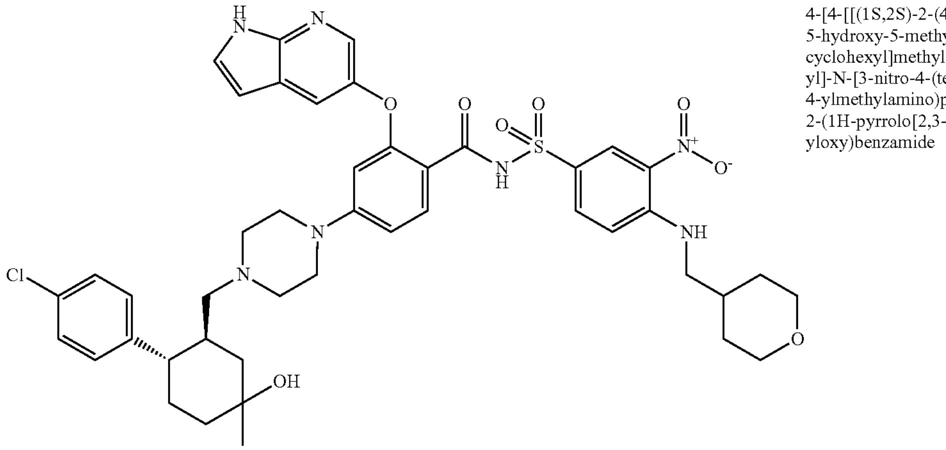 | 4-[4-[[(1S,2S)-2-(4-chlorophenyl)-5-hydroxy-5-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 31 | 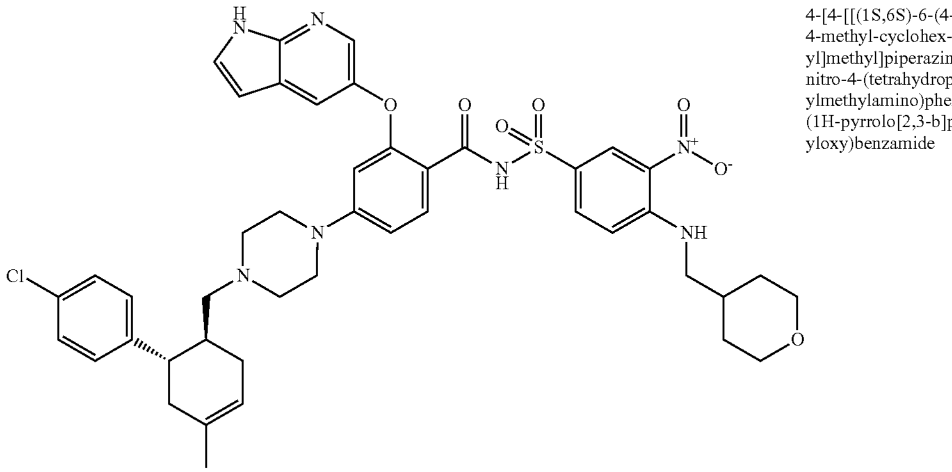 | 4-[4-[[(1S,6S)-6-(4-chlorophenyl)-4-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 52 | 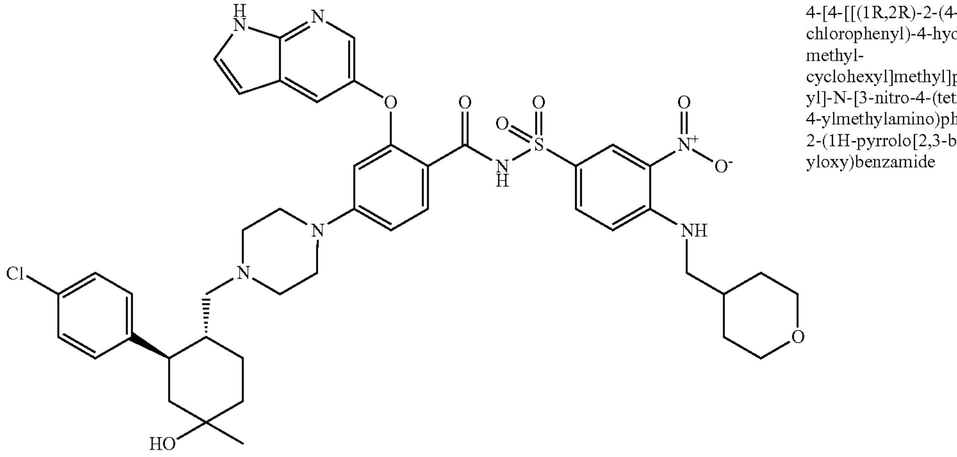 | 4-[4-[[(1R,2R)-2-(4-chlorophenyl)-4-hydroxy-4-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 53 | 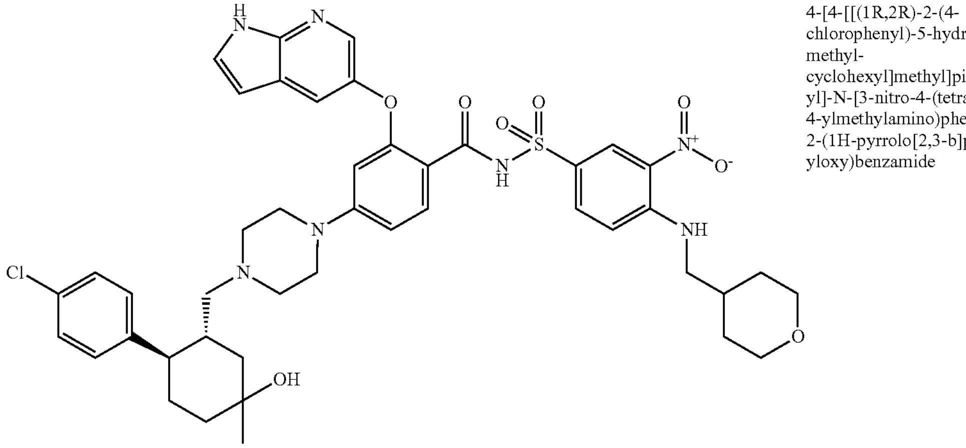 | 4-[4-[[(1R,2R)-2-(4-chlorophenyl)-5-hydroxy-5-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 54 | 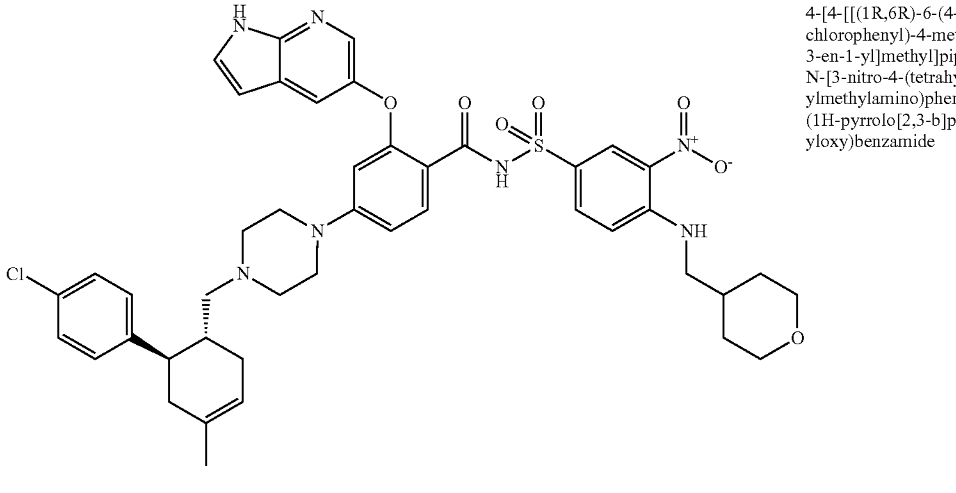 | 4-[4-[[(1R,6R)-6-(4-chlorophenyl)-4-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 60 | 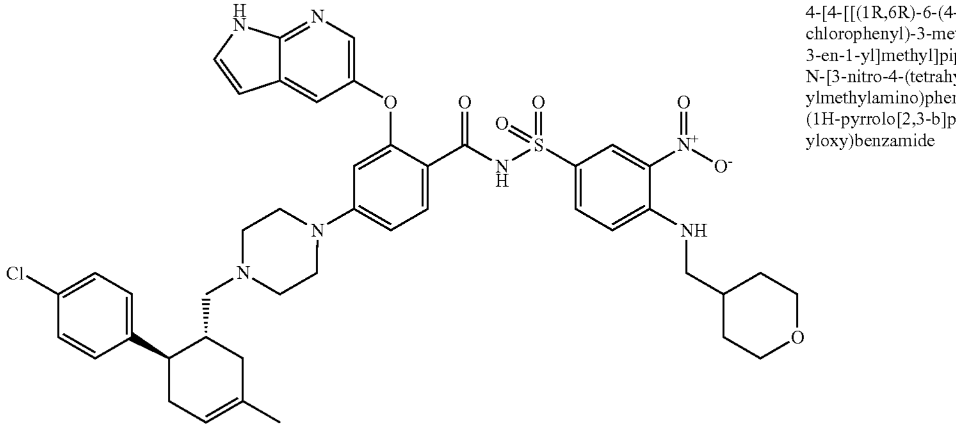 | 4-[4-[[(1R,6R)-6-(4-chlorophenyl)-3-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 67 | 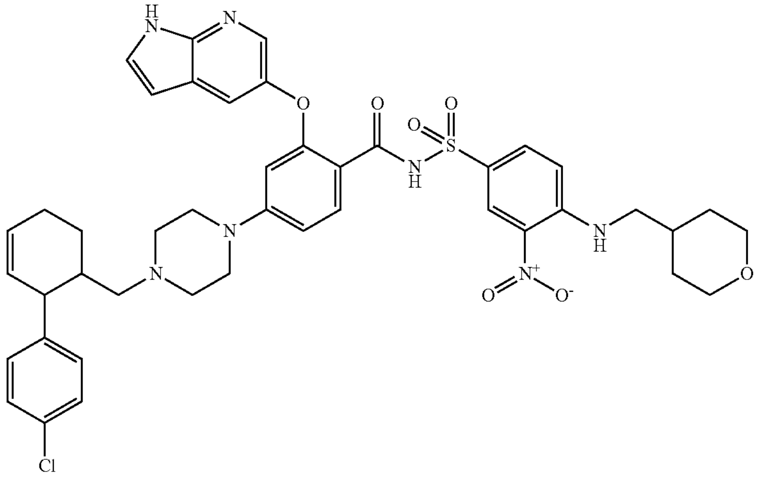 [SMILES: O=C(NS(=O)(=O)c1ccc(NCC2CCOCC2)c([N+](=O)[O-])c1)c1ccc(N2CCN(CC3CCC=CC3c3ccc(Cl)cc3)CC2)cc1Oc1cnc2[nH]ccc2c1] | 4-[4-[[2-(4-chlorophenyl)cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 71 | 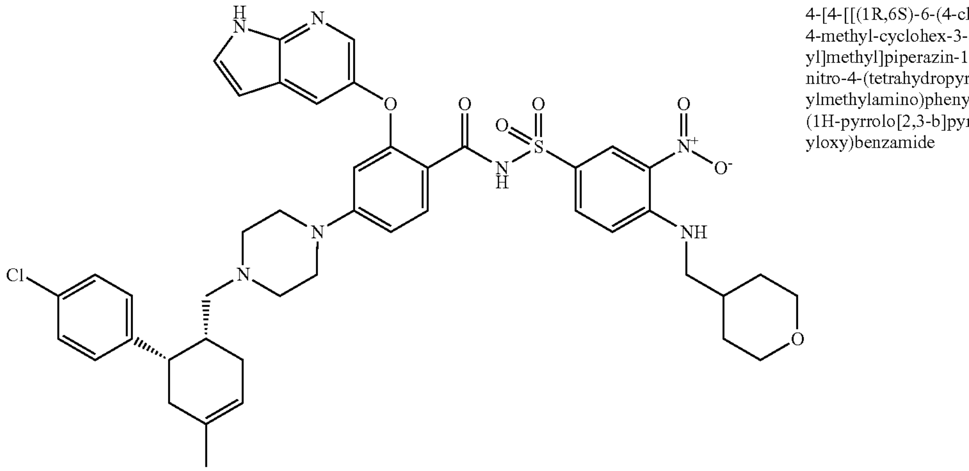 | 4-[4-[[(1R,6S)-6-(4-chlorophenyl)-4-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
| --- | --- | --- |
| 74 | 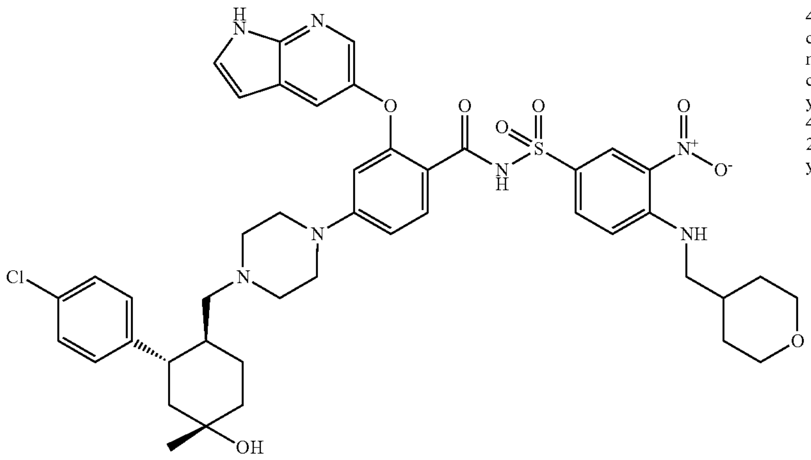 | 4-[4-[[(1S,2S,4S)-2-(4-chlorophenyl)-4-hydroxy-4-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 75 | 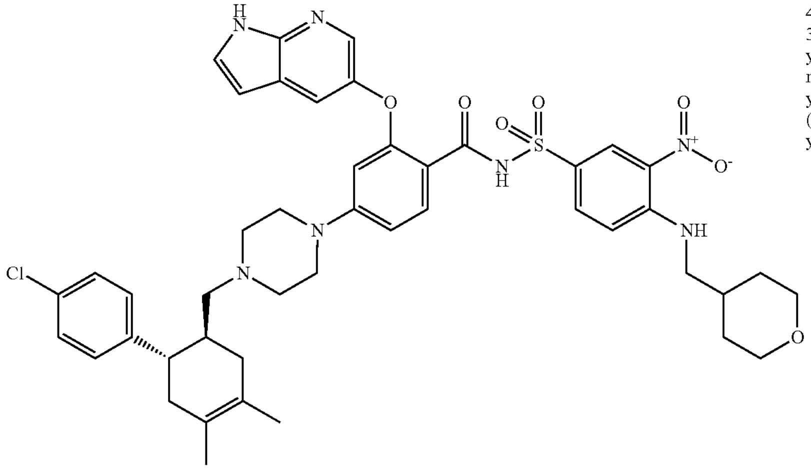 | 4-[4-[[(1S,6S)-6-(4-chlorophenyl)-3,4-dimethyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

and pharmaceutically acceptable salts, isomers, solvates, prodrugs, or tautomers thereof.

In some embodiments, the compound is a pharmaceutically acceptable salt. In some embodiments, the compound is a hydrochloride salt.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I)incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of BCL-2 proteins. In one embodiment, the compounds of the present invention are inhibitors of BCL-2 proteins. In another embodiment, the BCL-2 proteins is Isoform 1. In another embodiment, the BCL-2 proteins is Isoform 2.

In some embodiments, the compounds of Formula I are selective inhibitors of BCL-2 proteins.

In some embodiments, the compounds of Formula I are dual inhibitors of BCL-2/BCL-xL proteins.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (A) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Schemes A-F which comprise different sequences of assembling intermediates or compounds of Formulae I and I'. Starting materials are either commercially available or made by known procedures in the reported literature or as illustrated below.

Scheme A

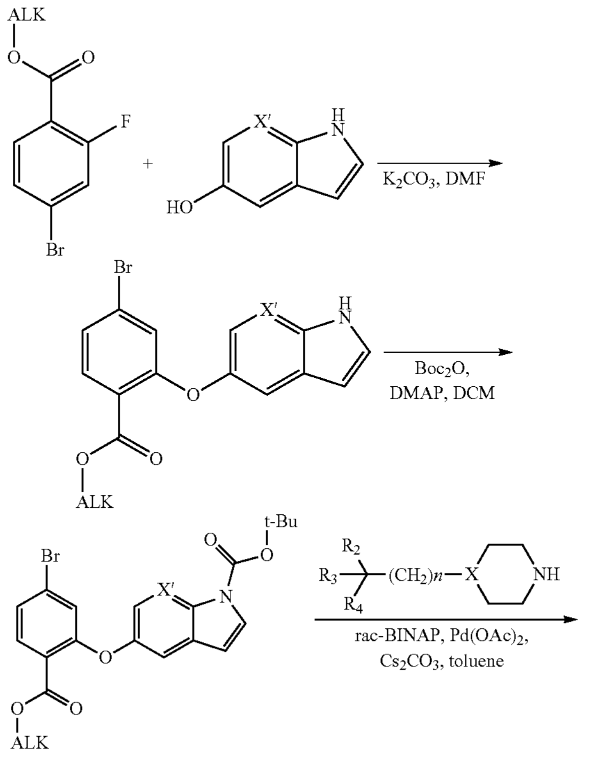

-continued

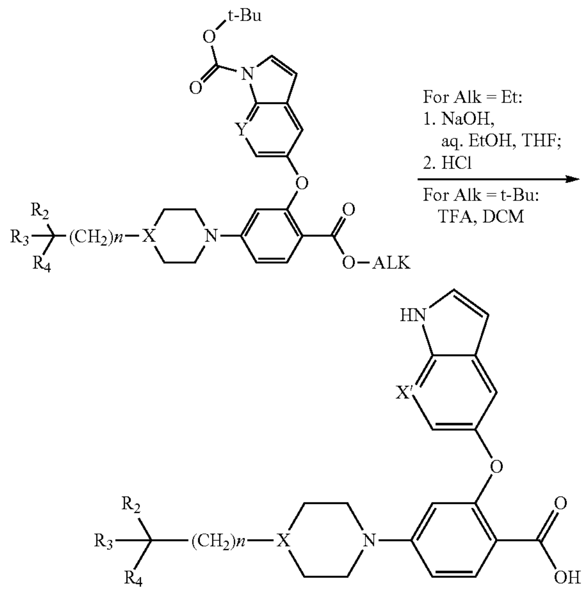

X' = CH, N
ALK = Et or t-Bu

Scheme B

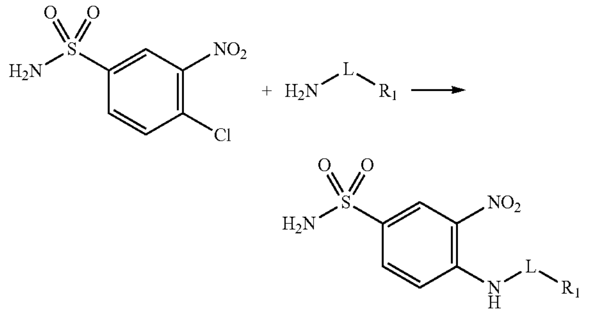

Scheme C

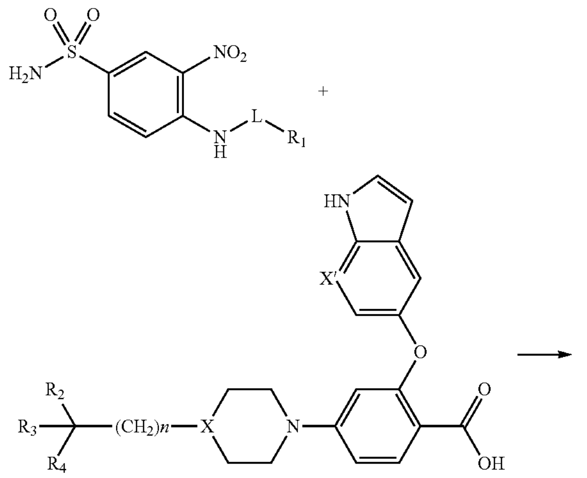

-continued

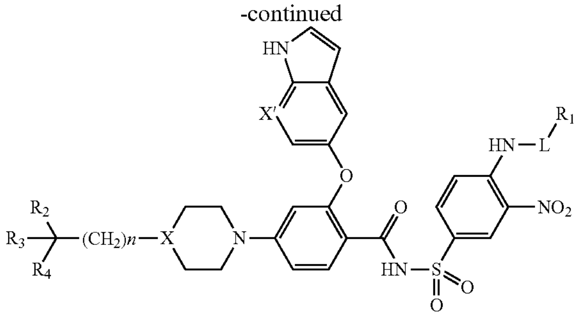

Methods of Using the Disclosed Compounds

Another aspect of the invention relates to a method of treating a disease or disorder associated with modulation of BCL-2 proteins. The method comprises administering to a patient in need of a treatment for diseases or disorders associated with modulation of BCL-2 proteins an effective amount the compositions and compounds of Formula (A).

In another aspect, the present invention is directed to a method of inhibiting BCL-2 proteins. The method involves administering to a patient in need thereof an effective amount of a compound of Formula (A).

Another aspect of the present invention relates to a method of treating, preventing, inhibiting or eliminating a disease or disorder in a patient associated with the inhibition of BCL-2 proteins, the method comprising administering to a patient in need thereof an effective amount of a compound of Formula (A). In one embodiment, the disease may be, but not limited to, cancer and metastasis.

The present invention also relates to the use of an inhibitor of BCL-2 proteins for the preparation of a medicament used in the treatment, prevention, inhibition or elimination of a disease or condition mediated by BCL-2 proteins, wherein the medicament comprises a compound of Formula (A).

In another aspect, the present invention relates to a method for the manufacture of a medicament for treating, preventing, inhibiting, or eliminating a disease or condition mediated by BCL-2 proteins, wherein the medicament comprises a compound of Formula (A).

Another aspect of the present invention relates to a compound of Formula (A) for use in the manufacture of a medicament for treating a disease associated with inhibiting BCL-2 proteins.

In another aspect, the present invention relates to the use of a compound of Formula (I) in the treatment of a disease associated with inhibiting BCL-2 proteins.

Another aspect of the invention relates to a method of treating cancer. The method comprises administering to a patient in need thereof an effective amount of a compound of Formula (A).

Another aspect of the invention relates to a method of treating or preventing cancer. The method comprises administering to a patient in need thereof an effective amount of a compound of Formula (A).

In one embodiment, the present invention relates to the use of an inhibitor of BCL-2 proteins for the preparation of a medicament used in treatment, prevention, inhibition or elimination of a disease or disorder associated with cancer.

In another embodiment, the present invention relates to a compound of Formula (A) or a pharmaceutical composition comprising a compound of the present invention and a pharmaceutically acceptable carrier used for the treatment of cancers including, but not limited to, bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, prostate cancer, marginal zone lymphoma (MZL), follicular lymphoma (FL), diffuse large B-cell lymphoma (DLBCL) and chronic lymphocytic leukemia/small lymphocytic lymphoma (CLL/SLL).

In another embodiment, the present invention relates to a compound of Formula (A) or a pharmaceutical composition comprising a compound of the present invention and a pharmaceutically acceptable carrier used for the treatment of cancers including, but not limited to, marginal zone lymphoma (MZL), follicular lymphoma (FL), diffuse large B-cell lymphoma (DLBCL) and chronic lymphocytic leukemia/small lymphocytic lymphoma (CLL/SLL).

Another aspect of the invention is directed to pharmaceutical compositions comprising a compound of Formula (A) and a pharmaceutically acceptable carrier. The pharmaceutical acceptable carrier may further include an excipient, diluent, or surfactant.

In one embodiment, are provided methods of treating a disease or disorder associated with modulation of BCL-2 proteins including, cancer or cell proliferative disorder, comprising administering to a patient suffering from at least one of said diseases or disorder a compound of Formula (A).

One therapeutic use of the compounds or compositions of the present invention which inhibit BCL-2 proteins is to provide treatment to patients or subjects suffering from a cancer or cell proliferative disorder.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (A) and a pharmaceutically acceptable carrier. The pharmaceutical acceptable carrier may further include an excipient, diluent, or surfactant. In some embodiments, the pharmaceutical composition can further comprise an additional pharmaceutically active agent.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations used in the following examples and elsewhere herein are:

atm atmosphere
br broad
anh. anhydrous
aq. aqueous
BINAP (2,2'-bis(diphenylphosphino)-1,1'-binaphthyl)
DCM dichloromethane (i.e. $CH_2Cl_2$)
DIPEA N,N-diisopropylethylamine
DMAP N,N-dimethylpyridin-4-amine
DMF N,N-dimethyl formamide
DMSO dimethyl sulfoxide
EDCI 1-(3-Dimethylaminopropyl)-3-ethylcarbodiimide
ESI electrospray ionization
h hour(s)
Hal halogen
HPLC high pressure (or performance) liquid chromatography
LCMS liquid chromatography mass spectrometry
m multiplet
M molar
MHz megahertz
min minutes
NMR nuclear magnetic resonance
ppm parts per million
rt room temperature
sat. saturated
STAB sodium triacetoxyborohydride
TFA trifluoroacetic acid
THF tetrahydrofuran
TLC thin layer chromatography Purity and identity of all synthesized compounds was confirmed by LC-MS analysis performed on Shimadzu Analytical 10Avp equipped with PE SCIEX API 165 mass, Sedex 75 ELSD, and Shimadzu UV (254 and 215) detectors. Separation was achieved with C18 column 100×4.6 mm, 5.0 μm, pore size 100 Å, water-acetonitrile+0.1% trifluoroacetic acid, gradient 5 to 87% for 10 min.

Preparative HPLC purification was carried out on Shimadzu instrument equipped with SPD-10Avp detector and FRC-10A fraction collector. Separation was achieved with a column YMC-Pack ODS-AQ 250×20 mml, S-10 μm, 12 nm, gradient solution A-solution B (A: 1000 mL water-226 μL trifluoroacetic acid; B: 1000 mL acetonitrile-226 μL trifluoroacetic acid).

3-Nitro-4-[(tetrahydro-2H-pyran-4-ylmethyl)amino]benzenesulfonamide and tert-butyl 4-bromo-2-(1H-pyrrolo[2,3-b]pyridin-5-yloxy)benzoate were synthesized according to reported procedure (US2014/275540).

EXAMPLES OF SYNTHESIS OF FINAL PRODUCTS

Synthesis of Compound P11

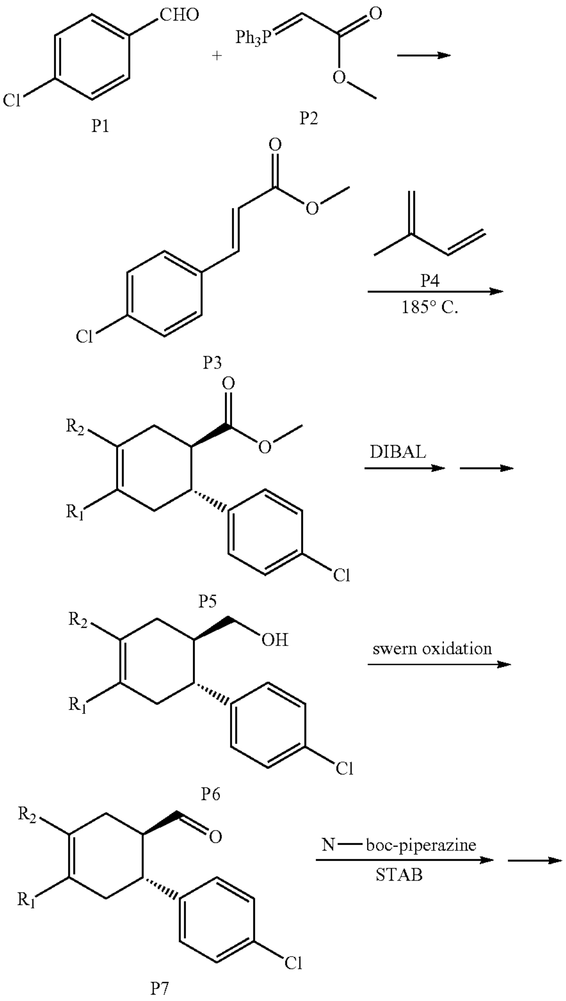

-continued

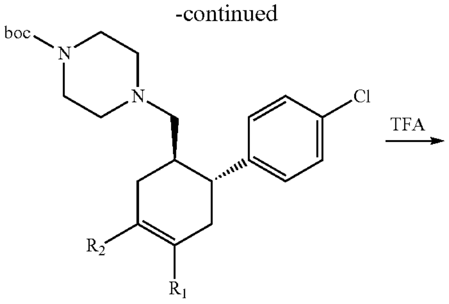

P8

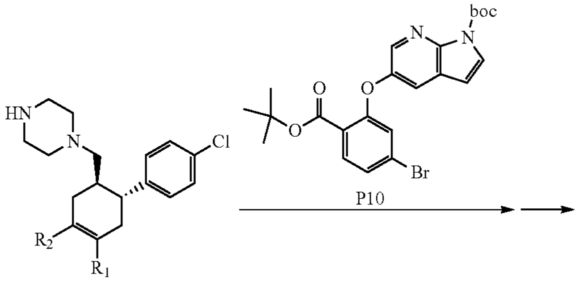

P10

P9

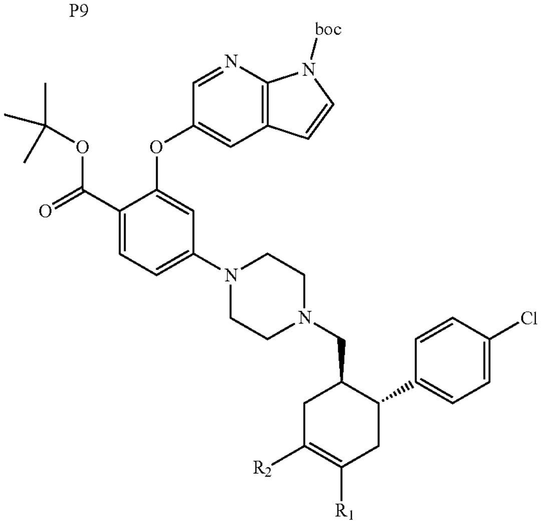

P11

$R_1$ = Me, $R_2$ = H (P5a, P6a, P7a, P8a, P9a, P11a)
$R_1$ = H, $R_2$ = Me (P5b, P6b, P7b, P8b, P9b, P11b)

Preparation 1. Compound P3.

p-Cl-benzaldehyde (10.54 g, 75.0 mmol) was added to a solution of P2 (33.8 g, 101 mmol) in DCM (400 mL) at rt. After stirring at same temperature overnight, the reaction mixture was evaporated under reduced pressure. The residue was purified by chromatography on silica gel with hexane/ethyl acetate (0→5%) as an eluent to afford compound P3 (11.1 g, 75%).

Preparation 2. Compound P5.

Isoprene (20.8 g, 285 mmol) was added to a solution of compound P3 (7.0 g, 35.6 mmol) in xylene (75 mL).The reaction mixture was heating in a round bottom flask pressure vessel at 185° C for 62 h and evaporated under reduced. The residue was purified by chromatography on silica gel with hexane/ethyl acetate (0→3%) as an eluent to afford compound P5 as a mixture of regioisomers (7.85 g, 83%).

Preparation 3. Compound P6.

To a stirred solution of compound P5 (4.23 g, 16.0 mmol) in toluene (150 mL) at −78° C, DIBAL (45 mL, 67.0 mmol) 25% solution in toluene was added portionwise. The reaction mixture was gradually warmed to 0° C, and stirred at same temperature for 1 h. Then aq. HCl (150 mL) and diethyl ether (350 mL) were slowly added. The organic layer was separated and washed with water, brine, dried with $Na_2SO_4$, and evaporated under reduced pressure. The residue (4.24 g) was purified by chromatography on silica gel with hexane/ethyl acetate (0→12%) as an eluent to afford compound P6 as a mixture of regioisomers (3.52 g, 95%).

Preparation 4. Compound P7.

To a stirred solution of oxalyl chloride (1.03 g, 8.08 mmol) and DMSO (1.29 g, 16.44 mmol) in DCM (15 mL) was added DCM solution (10 mL) of P6 (1.03 g, 4.35 mmol) at −78° C, and the mixture was stirred for 1 h. To this was added triethylamine (3.57 g, 35.2 mmol) dropwise for the period of 0.5 h and the mixture was gradually warmed up to rt for 1 h and sat. aq. $NH_4Cl$ (250 mL) and ethyl acetate (400 mL) were slowly added. The organic layer was separated and washed with aq. HCl(1%), brine, dried with $Na_2SO_4$, and evaporated under reduced pressure. The residue P7 (0.99 g, 97%) was used in the next step without additional purification.

Preparation 5. Compound P8.

To a solution of compound P7 (0.99 g, 4.21 mmol) in DCM (50 mL), N-boc-piperazine (0.83 g, 4.22 mmol) and AcOH (10 µl) was added. The reaction mixture was stirred at ambient temperature for 0.5 h, and STAB (2.69 g, 12.7 mmol) was added. The reaction mixture was stirred at ambient temperature overnight. After reaction completion (LC/MS monitoring), the mixture was quenched with sat. aq. $NaHCO_3$, organic layer was separated and washed with brine, dried with $Na_2SO_4$, and evaporated under reduced pressure. The residue (1.88 g) was purified by chromatography on silica gel with DCM/MeOH (0→1%) as an eluent to afford compound P8 as a mixture of regioisomers (1.43 g, 84%).

Preparation 6. Compound P9.

To a solution of compound P8 (1.43 g, 3.53 mmol) in DCM (30 mL) was added TFA (10 mL). The reaction mixture was stirred at rt for 1 h, and concentrated under reduced pressure. The residue (2.65 g) was dissolved in DCM (50 mL) and washed with sat. aq. $NaHCO_3$, dried with $Na_2SO_4$, and evaporated under reduced pressure. Compounds P9 (1.13 g, 100%) were used as a mixture in the next step without additional purification.

Preparation 7. Compound P11.

To a degassed (4x vacuum/purged with nitrogen) suspension of compound P9 (0.147 g, 0.485 mmol), $Cs_2CO_3$ (0.815 g, 2.50 mmol), BINAP (0.048 g, 0.077 mmol) and P10 (0.245 g, 0.5 mmol) in toluene (20 mL) was added $Pd(OAc)_2$ (0.015 g, 0.067 mmol). The reaction mixture was stirred at 80° C for 24 h, cooled to rt and filtered on a celite pad washed with AcOEt and concentrated under reduced pressure. The residue (2.65 g) was dissolved in DCM (50 mL) and washed with sat. aq. $NaHCO_3$, dried with $Na_2SO_4$, and evaporated under reduced pressure. The residue (0.418 g) was purified by chromatography on silica gel with hexane/ethyl acetate (0→20%) as an eluent to afford compound P11 as a mixture of regioisomeres (0.23 g, 67%).

Synthesis of Compounds P12, P13, P14
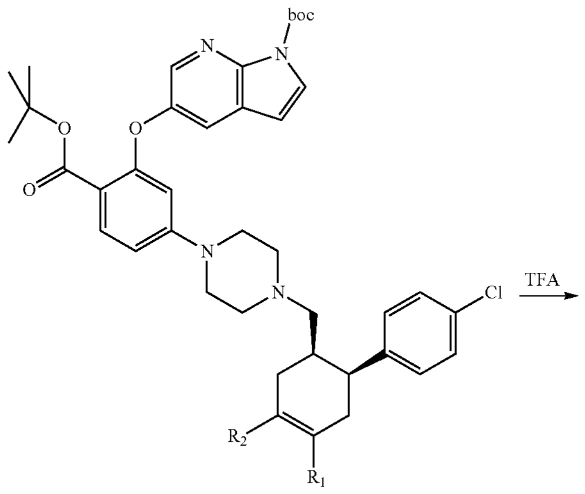
P11
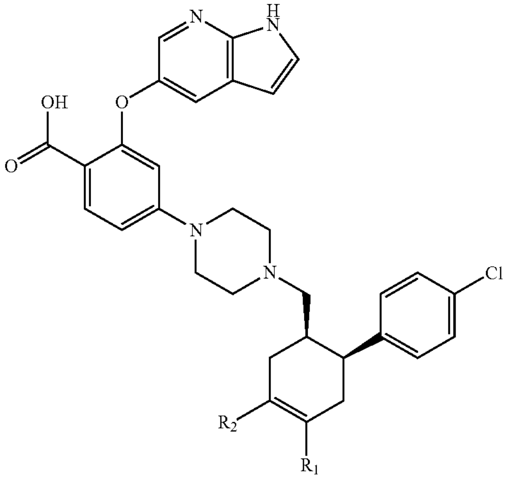
+
P12
-continued
+
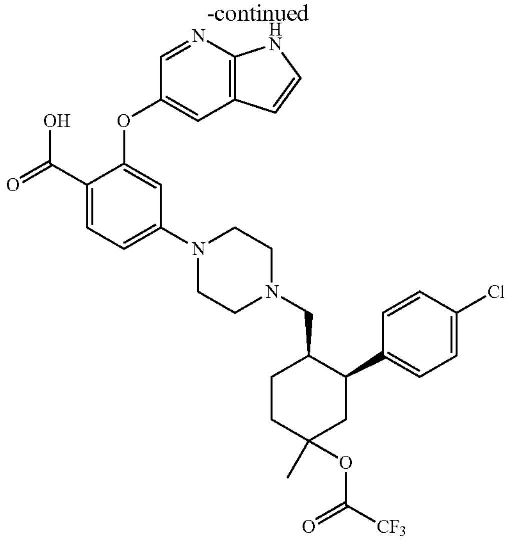
+
P13
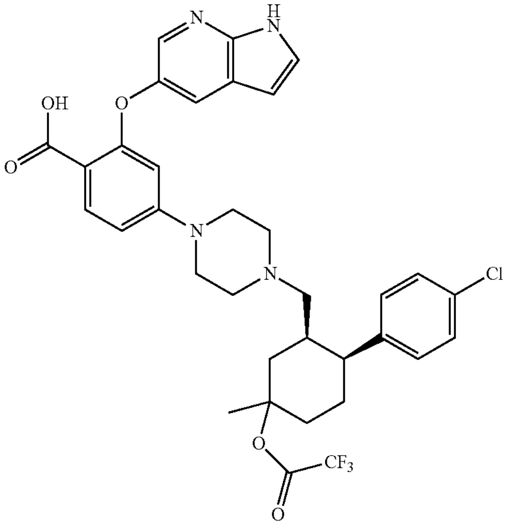
P14
Preparation 8. Compounds P12, P13, P14.
To a solution of compound P11 (0.173 g, 0.243 mmol) in DCM (18 mL) was added TFA (8 mL). The reaction mixture was stirred at rt overnight, and concentrated under reduced pressure, dried in vacuum at 50° C to afford mixture of P12, P13, P14 (0.24 g, 100%) as a powder.

Synthesis of Compounds 28, 29, 54, 60

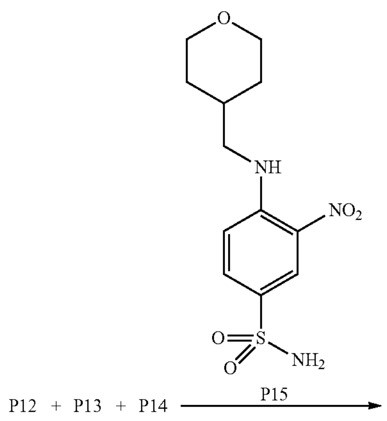

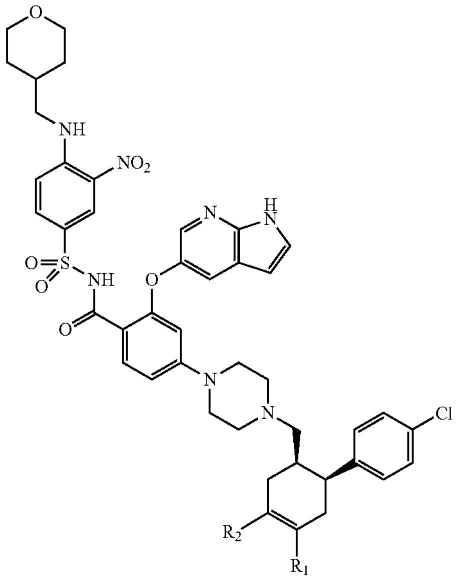

54, 60

+

-continued

+

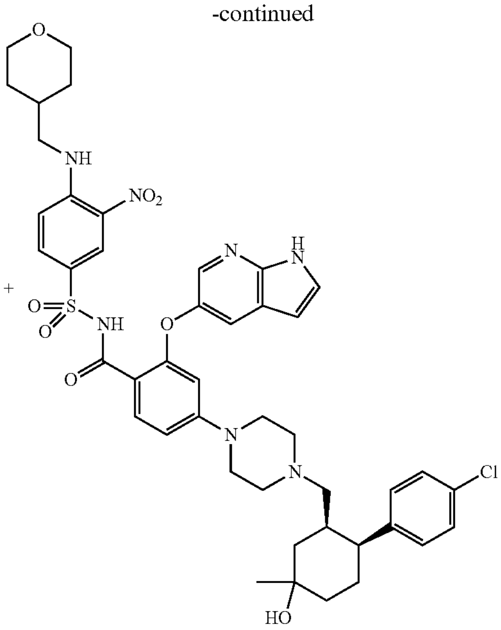

29

+

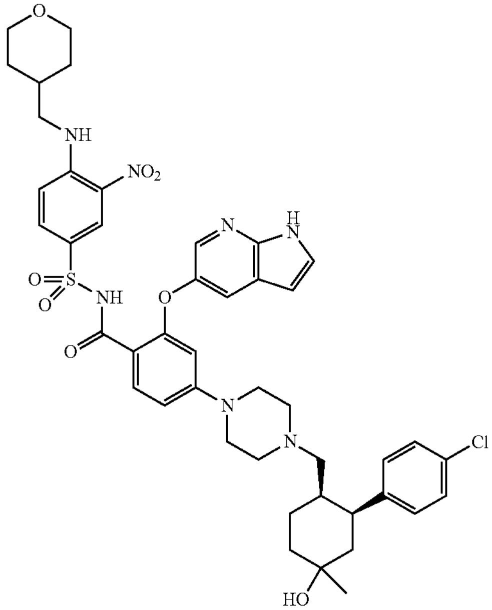

28

Preparation 9. Compounds 28, 29, 54, 60.

To a solution of mixture P12, P13, P14 (0.23 g), P15 (0.082 g, 0.26 mmol), DMAP (0.045 g, 0.37 mmol) and $Et_3N$ (0.19 g, 1.88 mmol) in DCM (10 mL) was added EDCI (0.071 g, 0.37 mmol). The reaction mixture was stirred at ambient temperature overnight. After reaction completion (LCMS monitoring), the mixture was quenched with water, organic layer was separated and washed with brine, dried with $Na_2SO_4$, and evaporated under reduced pressure. The residue (0.286 g) was purified on preparative HPLC to afford compounds 54 and 60 (55 mg), 28 (21 mg), 29 (13 mg).

Synthesis of Compound 67
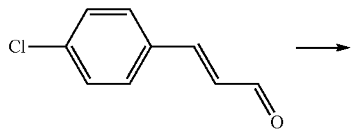
P16
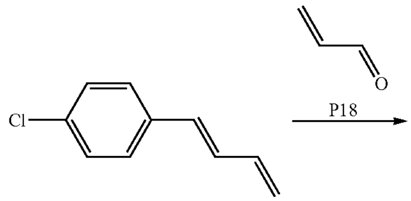
P18
P17
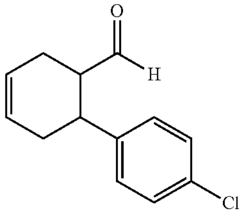
P19
+
+
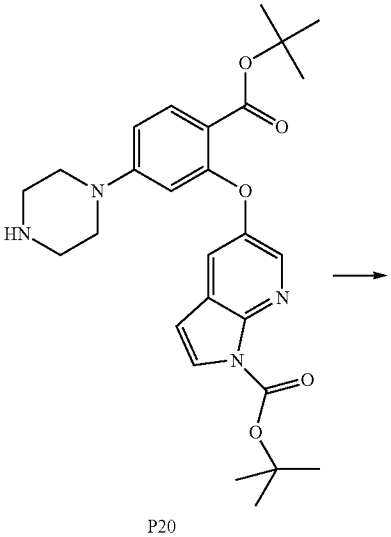
P20
-continued
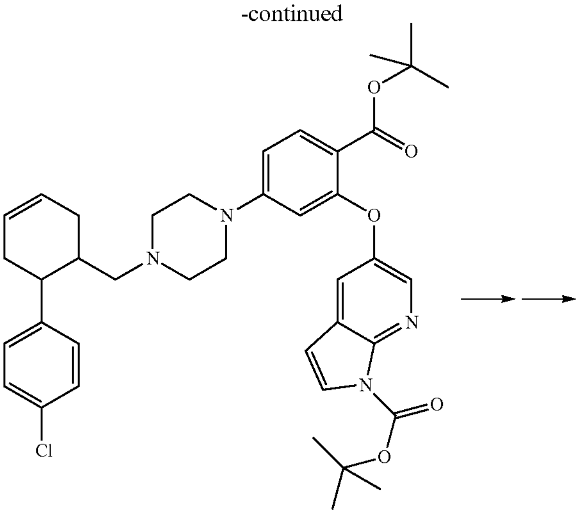
P21
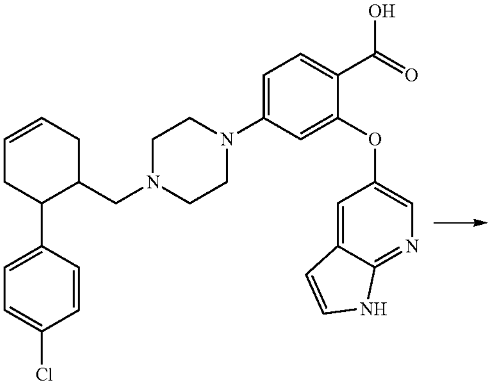
P22
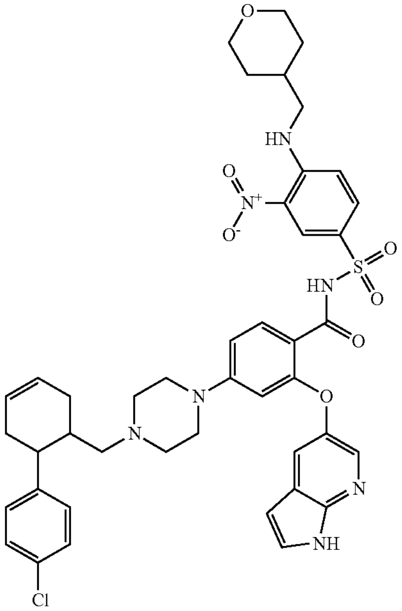
67
Preparation 10. Compound P17.
A suspension of methyltriphenylphosphonium iodide (2.66 g, 6.6 mmol) and potassium tert-butoxide (0.77 g, 6.9 mmol) in anh. THF (35 ml) was stirred for 10 min at 0° C under a nitrogen atmosphere. The reaction mixture was then treated with trans p-chlorophenyl-cinnamaldehyde (1 g, 6 mmol) and stirred for 5 h under reflux. Upon completion, the mixture was diluted with hexanes (50 ml) and the solid phosphine oxide was removed by filtration. The solvent was reduced under vacuum and the product was extracted from the gummy residue with n-hexanes (3×40 ml). Evaporation of the solvents under reduced pressure gave an oily residue which was purified by column chromatography to give 1-p-chlorophenyl-1,3-butadiene (0.75 g, 76%). $^1$H NMR (400 MHz), δ: 7.50 (2H, d, J=8.4), 7.38 (2H, d, J=8.4), 6.93 (1H, dd, J=10.8, 15.6), 6.63 (1H, d, J=17.6), 6.5 (1H, m), 5.37 (1H, d, J=17.2), 5.23 (1H, d, J=10.0). LCMS (ESI)$^+$ m/z 165.5 [M−H]$^+$.

Preparation 11. Compound P19.

A solution of 1-p-chlorophenyl-1,3-butadiene (0.7 g, 4.25 mmol), acrolein (0.47 g, 8.5 mmol) and hydroquinone (0.045 g, 0.4 mmol) was reflux for 72 h under a nitrogen atmosphere. The solvent was removed under vacuum and the residue was purified by column chromatography (hexane:DCM; 2:1) to give a mixture of cis-, trans-6-(4-chlorophenyl)cyclohex-3-enecarbaldehydes (0.35 g, 37%). $^1$H NMR (400 MHz), δ: 9.59 (1H, s), 7.42-7.3 (2H, m), 7.28-7.18 (2H, m), 6.02-5.95 (0.5H, m), 5.92-5.81 (0.5H, m), 5.80-5.71 (0.5H, m), 5.62-5.71 (0.5H, m), 4.17-4.1 (0.5H, m), 3.81-3.75 (0.5H, m), 2.95-2.85 (0.5H, m), 2.65-2.55 (0.5H, m), 2.3-2(2H, m). 1.92-1.4 (2H, m). LCMS (ESI)$^+$ m/z 221.5 [M−H]$^+$.

Preparation 12. Compound P21.

To a solution of 6-(4-chlorophenyl)cyclohex-3-enecarbaldehyde P19 (0.27 g, 1.2 mmol) and tert-butyl 5-(2-(tert-butoxycarbonyl)-5-(piperazin-1-yl)phenoxy)-1H-pyrrolo[2,3-b]pyridine-1-carboxylate P20 (0.6 g, 1.2 mmol) in anh. DCM (7 ml) was added STAB (0.52 g, 2.44 mmol) and the reaction mixture was stirred for 24 h at rt. Upon completion, the mixture was diluted with the saturated solution of $NH_4Cl$ (10 ml), the organic phase was separated. The solvent was evaporated under vacuum and the tert-butyl 5-(2-(tert-butoxycarbonyl)-5-(4-((6-(4-chlorophenyl)cyclohex-3-enyl)methyl)piperazin-1-yl)phenoxy)-1H-pyrrolo[2,3-b]pyridine-1-carboxylate P21 was used in next step without purification (0.8 g, 93%; crude). LCMS (ESI)$^+$ m/z 700 [M+H]$^+$.

Preparation 12. Compound P22.

tert-Butyl 5-(2-(tert-butoxycarbonyl)-5-(4-((6-(4-chlorophenyl)cyclohex-3-enyl)methyl)piperazin-1-yl)phenoxy)-1H-pyrrolo[2,3-b]pyridine-1-carboxylate P21 (0.8 g, 1.1 mmol), was dissolved in DCM (20 ml), 3 M solution of HCl in dioxane (5 ml) was added to the reaction mixture and stirred at rt overnight. The solvent was removed under vacuum to dryness and 2-(1H-pyrrolo[2,3-b]pyridin-5-yloxy)-4-(4-((6-(4-chlorophenyl)cyclohex-3-enyl)methyl)piperazin-1-yl)benzoic acid P22 was used in next step without purification (0.7 g, 93%; crude). LCMS (ESI)$^+$ m/z 600 [M−H]$^+$.

Preparation 13. Compound 67.

A mixture of 2-(1H-pyrrolo[2,3-b]pyridin-5-yloxy)-4-(4-((6-(4-chlorophenyl)cyclohex-3-enyl)methyl)piperazin-1-yl)benzoic acid P22 (0.1 g, 0.172 mmol), 4-nitro-3-[(tetrahydro-2H-pyran-4-ylmethyl)amino]benzenesulfonamide (0.065 g, 0.2 mmol), EDCI (0.102 g, 0.533 mmol), DMAP (0.063 g, 0.51 mmol) and $Et_3N$ (0.25 ml, 1.77 mmol) in DCM (10 ml) was stirred at rt for 12 h, then the reaction mass was washed with water, the organic layer was dried over $Na_2SO_4$ the solvent was removed under reduced pressure, the residue was purified by HPLC. Yield of 2-(1H-pyrrolo[2,3-b]pyridin-5-yloxy)-4-(4-((2-(4-chlorophenyl)cyclohex-3-enyl)methyl)piperazin-1-yl)-N-(3-nitro-4-((tetrahydro-2H-pyran-4-yl)methylamino)phenylsulfonyl)benzamide: 0.054 g (37%). LCMS (ESI)$^+$ m/z 841 [M−H]$^+$.

Results of $^1$H-NMR analysis for certain compounds of the presented invention are presented in the Table 1.

TABLE 1

$^1$H-NMR specters description for certain compounds of the disclosure

| Cmpd No. | Structure | $^1$H-NMR |
|---|---|---|
| 67 | 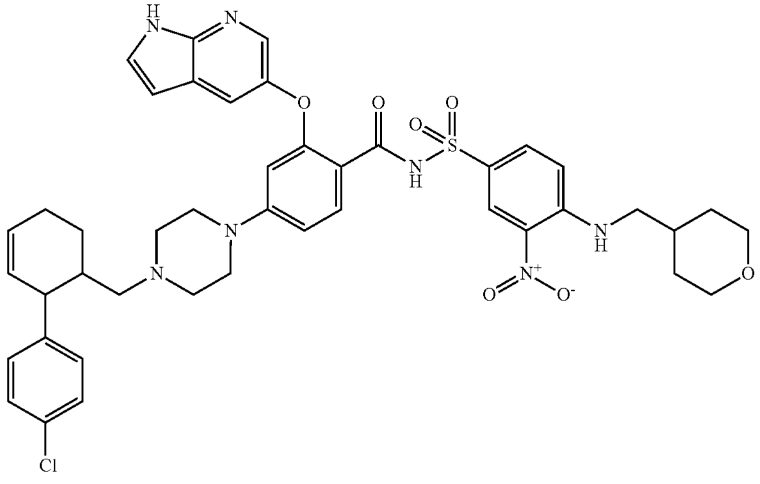 [SMILES: O=C(NS(=O)(=O)c1ccc(NCC2CCOCC2)c([N+](=O)[O-])c1)c1ccc(N2CCN(CC3CCC=CC3c3ccc(Cl)cc3)CC2)cc1Oc1cnc2[nH]ccc2c1] | $^1$H NMR (400 MHz, DMSO-d$_6$), δ: 11.69 (s, 2H), 9.15 (s, 1H), 8.61 (t, J = 6.0 Hz, 1H), 8.56 (t, J = 1.8 Hz, 1H), 8.04 (m, 1H), 7.80 (dd, J = 9.3, 2.3 Hz, 1H), 7.54 (m, 2H), 7.51 (m, 1H), 7.38 (m, 2H), 7.22 (m, 2H), 7.12 (d, J = 9.4 Hz, 1H), 6.79 (m, 1H), 6.38 (m, 1H), 6.32 (m, 1H), 5.90 (m, 1H), 5.60 (m, 1H), 3.85 (m, 4H), 3.48 (m, 2H), 3.28 (m, 4H), 3.08 (m, 6H), 2.13 (m, 2H), 1.82 (m, 2H), 1.61 (d, J = 12.9 Hz, 2H), 1.22 (m, 4H) |

TABLE 1-continued

| $^1$H-NMR specters description for certain compounds of the disclosure | | |
|---|---|---|
| Cmpd No. | Structure | $^1$H-NMR |
| 71 | 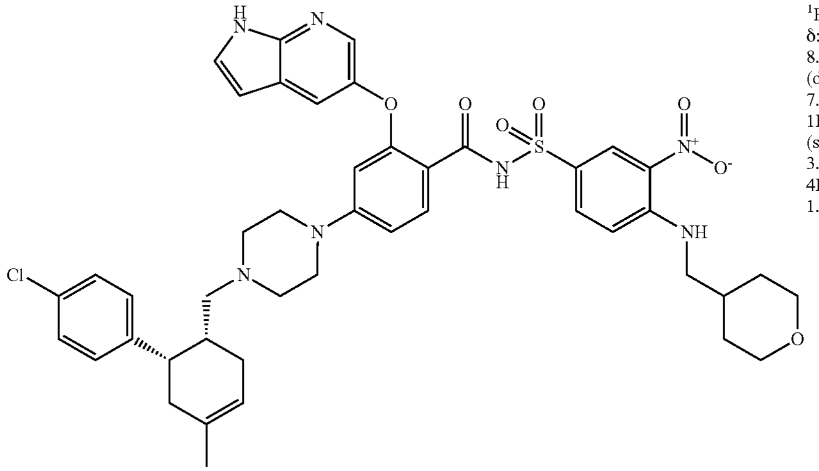 | $^1$H NMR (400 MHz, DMSO-$d_6$), δ: 11.68 (s, 1H), 11.31 (s, 1H), 8.57 (m, 2H), 8.03 (s, 1H), 7.78 (d, J = 9.1 Hz, 1H), 7.50 (m, 3H), 7.25 (m, 4H), 7.09 (d, J = 9.4 Hz, 1H), 6.69 (d, J = 9.6 Hz, 1H), 6.38 (s, 1H), 6.19 (s, 1H), 5.40 (s, 1H), 3.84 (m, 2H), 3.32 (s, 4H), 3.07 (s, 4H), 2.04 (m, 11H), 1.61 (m, 6H), 1.25 (m, 3H) |
| 74 | 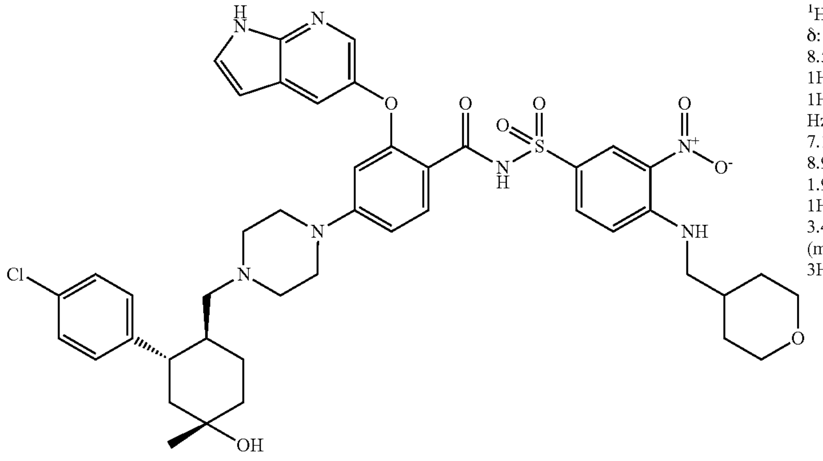 | $^1$H NMR (400 MHz, DMSO-$d_6$), δ: 11.66 (m, 2H), 9.01 (s, 1H), 8.58 (m, 2H), 8.03 (d, J = 2.6 Hz, 1H), 7.80 (dd, J = 9.5, 2.3 Hz, 1H), 7.52 (m, 3H), 7.34 (d, J = 8.1 Hz, 2H), 7.23 (d, J = 8.1 Hz, 2H), 7.11 (d, J = 9.3 Hz, 1H), 6.74 (d, J = 8.9 Hz, 1H), 6.38 (dd, J = 3.5, 1.9 Hz, 1H), 6.29 (d, J = 2.3 Hz, 1H), 3.85 (m, 2H), 3.69 (m, 2H), 3.49 (m, 1H), 3.28 (m, 5H), 2.97 (m, 4H), 2.67 (m, 2H), 1.95 (m, 3H), 1.58 (m, 6H), 1.21 (m, 6H) |
| 75 | 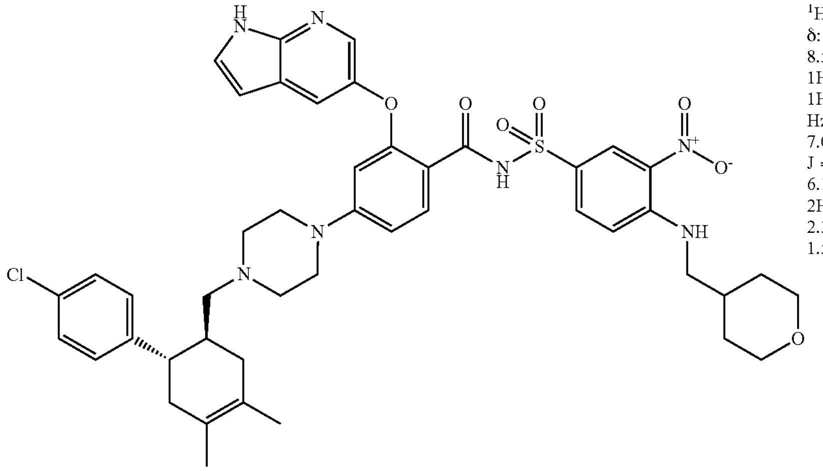 | $^1$H NMR (400 MHz, DMSO-$d_6$), δ: 11.67 (s, 1H), 11.39 (s, 1H), 8.56 (m, 2H), 8.03 (d, J = 2.6 Hz, 1H), 7.78 (dd, J = 9.2, 2.3 Hz, 1H), 7.50 (m, 3H), 7.29 (d, J = 8.1 Hz, 2H), 7.20 (d, J = 8.2 Hz, 2H), 7.08 (d, J = 9.3 Hz, 1H), 6.68 (dd, J = 9.0, 2.3 Hz, 1H), 6.38 (m, 1H), 6.19 (d, J = 2.3 Hz, 1H), 3.85 (m, 2H), 3.30 (m, 2H), 3.06 (s, 4H), 2.38 (m, 2H), 1.67-2.24 (m, 13H), 1.58 (m, 8H), 1.23 (m, 2H) |

Example A. Primary PPI Inhibition Assays

BCL-2 TR-FRET Assay (BPS Bioscience, #50222) Assay Condition: The following assay concentrations and times were used: 3 ng BCL-2, 5 ul of 1:100 anti-His Tb-labeled donor, 5 ul of 1:100 Dye-labeled acceptor, 5 ul of 1:40 BCL-2 Peptide Ligand, and 2 ul of test compound, with 60 min incubation time. The results of the assay were read using a Clariostar (BMG Labtech) plate reader with the following parameters: TR FRET, 340ex/620 and 665em; 60 μsec Delay; and 500 μsec integration.

BCL-XL TR-FRET Assay (BPS Bioscience, #50223) Assay Condition: The following assay concentrations and times were used: 10.5 ng BCL-XL, 5 ul of 1:100 anti-His Tb-labeled donor, 5 ul of 1:100 Dye-labeled acceptor, 5 ul of 1:80 BCL-XL Peptide Ligand, and 2 ul of test compound, with 60 min incubation time. The results of the assay were read using a Clariostar (BMG Labtech) plate reader with the following parameters: TR FRET, 340ex/620 and 665em; 60 μsec Delay; and 500 μsec integration.

MCL-1 TR-FRET Assay (BPS Bioscience, #79506) Assay Condition: The following assay concentrations and times were used: 10 ng MCL-1, 5 ul of 1:200 anti-His Tb-labeled donor, 5 ul of 1:200 Dye-labeled acceptor, 5 ul of 1:10 MCL-1 Peptide Ligand, and 2 ul of test compound, with 60 min incubation time. The results of the assay were read using a Clariostar (BMG Labtech) plate reader with the following parameters: TR FRET, 340ex/620 and 665em; 60 μsec Delay; and 500 μsec integration.

Table A assigns a code for potency for BCL-2 TR-FRET Assay: A, B, C, or D. According to the code, A represents an $IC_{50}$ value ≤5 nM; B represents $IC_{50}$>5 nM and ≤10 nM; C represents $IC_{50}$>10 nM and ≤50 nM D represents $IC_{50}$>50 nM.

Table A assigns a code for potency for BCL-XL TR-FRET Assay: A, B, or C. According to the code, A represents $IC_{50}$ value ≤2,000 nM; B represents $IC_{50}$ values >2,000 nM and ≤4,000 nM; C represents $IC_{50}$ values >4,000 nM.

TABLE A

| Primary PPI inhibition | | |
|---|---|---|
| Compound No. | BCL2 | BCLxL |
| 28 | A | A |
| 52 | B | A |
| 54 | C | B |
| 60 | D | C |
| 67 | C | N/A |
| 71 | C | C |
| 74 | C | B |
| 75 | D | A |

Example B. Cell Viability Assays (Cell lines HEK293, RS4-11, MOLT-4)

Assay Condition: Used culture medium for HEK293-DMEM (PanEco, Cat # C420), for the rest of the cell lines—culture medium RPMI-1640 (PanEco, Cat # C363).

Assay Procedure: Compounds were prepared as 200x stocks with serial dilution in 100% DMSO with a final concentration of 1x. Dispersed 40 μl in 384-well plates at a concentration of 2000 cells per well for HEK293 and at a concentration of 4000 cells per well for the rest of the cell lines using a robotic station Biomek (Beckman). Before adding compounds, the cells were incubated at 37° C (HEK293 were incubated for a day before adding compounds).

A dilution plate was prepared by pouring 78 μl of the appropriate culture medium using a robotic station Biomek (Beckman). Sequentially, using a robotic station, 2 μl of substances were taken and added to 78 μl of culture medium (dilution of compounds 40x). Took from there 10 μl and added to the plates to the cells (dilution of compounds 5x). The plates were incubated for 3 days at a temperature 37° C After 3 days, 10 μl of CellTiter-Glo (Promega) was added to the cells and the luminescence was measured.

Table B assigns a code for potency for RS4-11 Assay: A, B, or C. According to the code, A represents an $CC_{50}$ value ≤0.1 μM; B represents $CC_{50}$>0.1 μM and ≤0.2 μM; C represents $CC_{50}$>0.2 μM.

Table B assigns a code for potency for MOLT-4 Assay: A, B, or C. According to the code, A represents an $CC_{50}$ value ≤2 μM; B represents $CC_{50}$>2 μM and ≤10 μM; C represents $CC_{50}$>10 μM.

Table B assigns a code for potency for HEK293 Assay: A, B, or C. According to the code, A represents an $CC_{50}$ value ≤10 μM; B represents $CC_{50}$>10 μM and ≤25 μM; C represents $CC_{50}$>25 μM.

TABLE B

| Cellular models efficacy and cytotoxicity. | | | |
|---|---|---|---|
| Compound No. | RS4-11 | MOLT-4 | HEK293 |
| 28 | B | B | C |
| 31 | B | B | B |
| 52 | A | B | B |
| 53 | C | C | C |
| 54 | B | B | B |
| 74 | C | B | B |
| 75 | C | B | C |

Example C. Cas-3/7 Activation

Assay Principle: The Caspase-Glo 3/7 Assay is homogeneous, luminescent assay that measures caspase-3 and -7 activities. The assay provides a luminogenic caspase-3/7 substrate, which contains the tetrapeptide sequence DEVD, in a reagent optimized for caspase activity.

Assay Procedure: Incubate RS4-11 cells with varying concentrations of test compounds for 3.5 h in a humidified incubator at 37° C and 5% $CO_2$ and 30 min at r.t. Add 15 μl Caspase-Glo reagent to each well and incubate the plate for 30 min at r.t. Read on ClarioStar Plus instrument.

Materials: Promega Caspase-Glo (Promega, #8212); Frozen RS4-11 cells; 384-well white plate (Corning, #3570).

Instrumentation: ClarioStar Plus; Biomek FX for liquid handling (Beckman Coulter).

Table C assigns a code for potency for Cas-3/7 Assay: A, B, or C. According to the code, A represents an $EC_{50}$ value ≤0.1 μM; B represents $EC_{50}$>0.1 μM and ≤0.25 μM; C represents $EC_{50}$>0.25 μM.

TABLE C

| Caspase-3/7 activation | |
|---|---|
| Compound No. | Cas-37 |
| 28 | B |
| 31 | B |
| 52 | A |
| 53 | C |
| 54 | B |
| 67 | C |
| 75 | C |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of Formula (A):

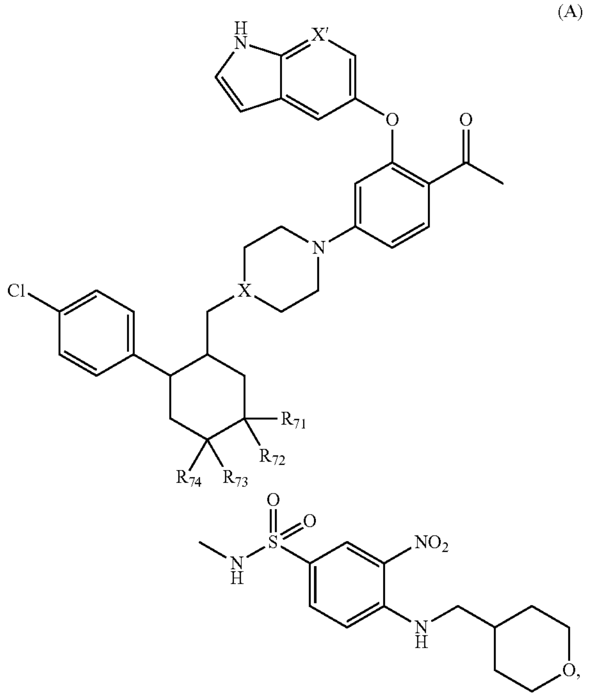

(A)

or pharmaceutically acceptable salts, solvates, or tautomers thereof, wherein:

X is selected from N and CH;

X' is selected from N and CH;

$R_{71}$ is selected from H, $C_1$-$C_6$ alkyl;

$R_{72}$ and $R_{73}$ are independently selected from H and OH, with the proviso that at least one from $R_{72}$ and $R_{73}$ is OH, or $R_{72}$ and $R_{73}$ together form a bond; and $R_{74}$ is selected from H, $C_1$-$C_6$ alkyl.

2. The compound of claim 1, wherein Formula (A) is a compound of Formula (A-I):

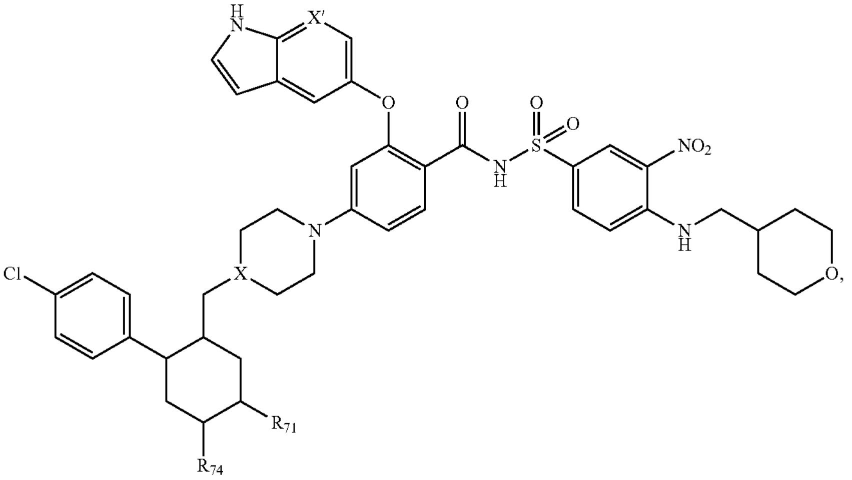

(A-I)

or pharmaceutically acceptable salts, solvates, or tautomers thereof.

3. A compound selected from:

| Compound No | Structure | Name |
|---|---|---|
| 28 | 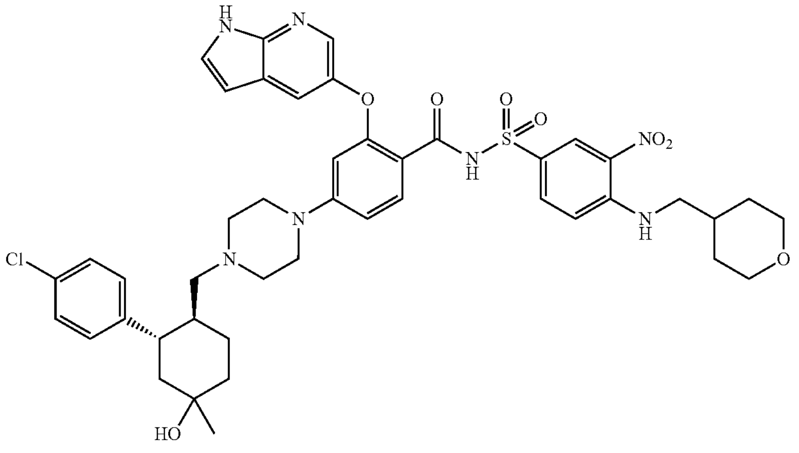 [SMILES: CC1(O)CC[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)C1] | 4-[4-[[(1S,2S)-2-(4-chlorophenyl)-4-hydroxy-4-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 29 | 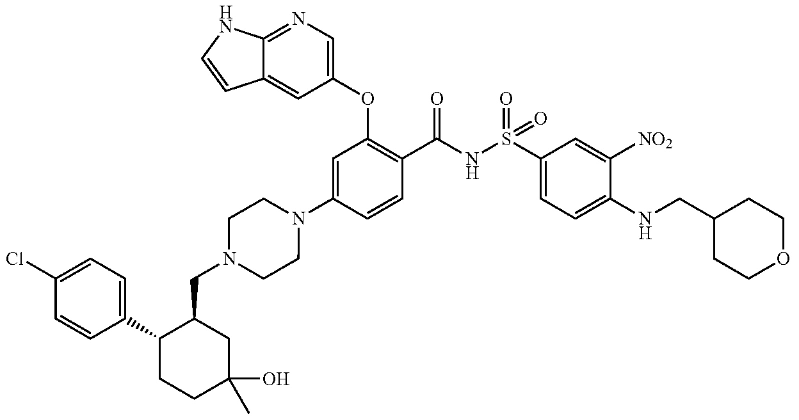 [SMILES: CC1(O)CC[C@H](c2ccc(Cl)cc2)[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)C1] | 4-[4-[[(1S,2S)-2-(4-chlorophenyl)-5-hydroxy-5-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 31 | 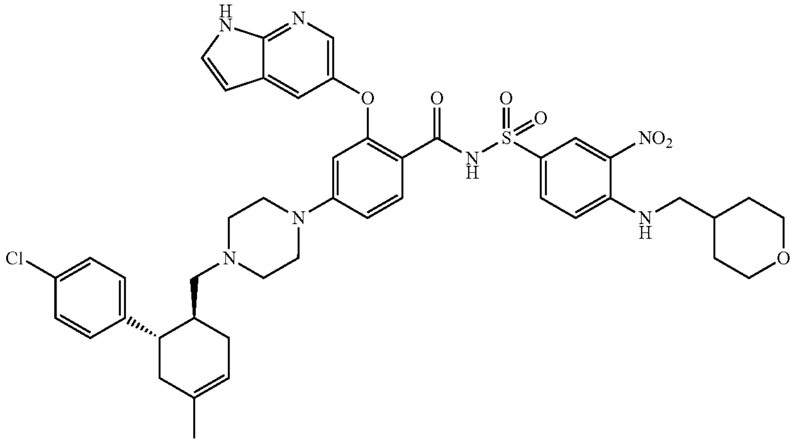 [SMILES: CC1=CC[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)C1] | 4-[4-[[(1S,6S)-6-(4-chlorophenyl)-4-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
| --- | --- | --- |
| 52 | 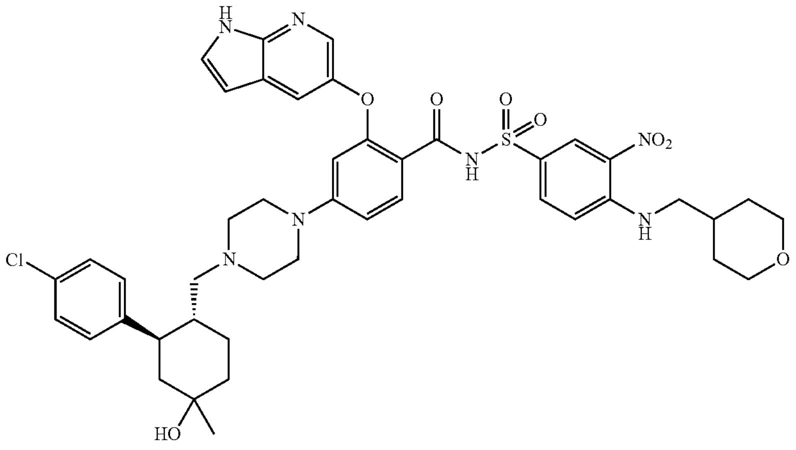 [SMILES: CC1(O)CC[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@H](c2ccc(Cl)cc2)C1] | 4-[4-[[(1R,2R)-2-(4-chlorophenyl)-4-hydroxy-4-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 53 | 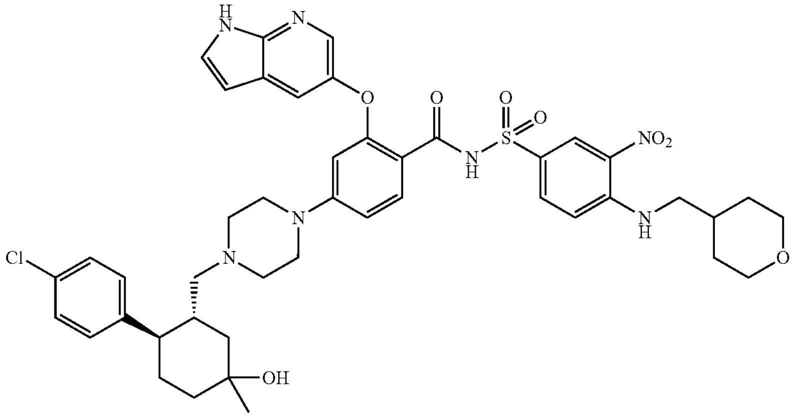 [SMILES: CC1(O)CC[C@@H](c2ccc(Cl)cc2)[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)C1] | 4-[4-[[(1R,2R)-2-(4-chlorophenyl)-5-hydroxy-5-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 54 | 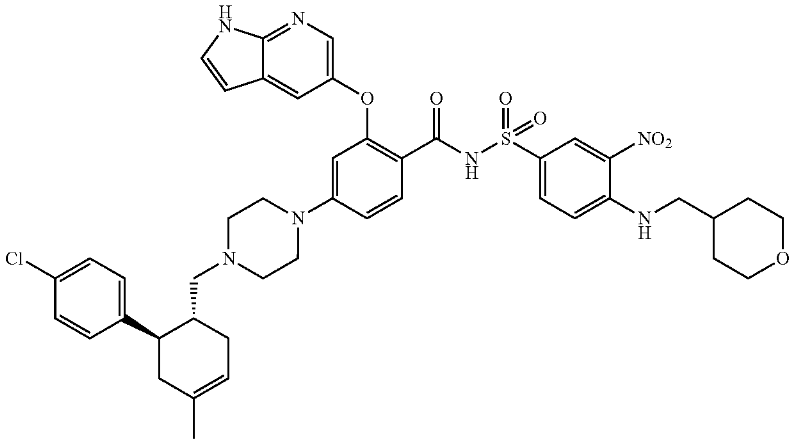 [SMILES: CC1=CC[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@H](c2ccc(Cl)cc2)C1] | 4-[4-[[(1R,6R)-6-(4-chlorophenyl)-4-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
|---|---|---|
| 60 | 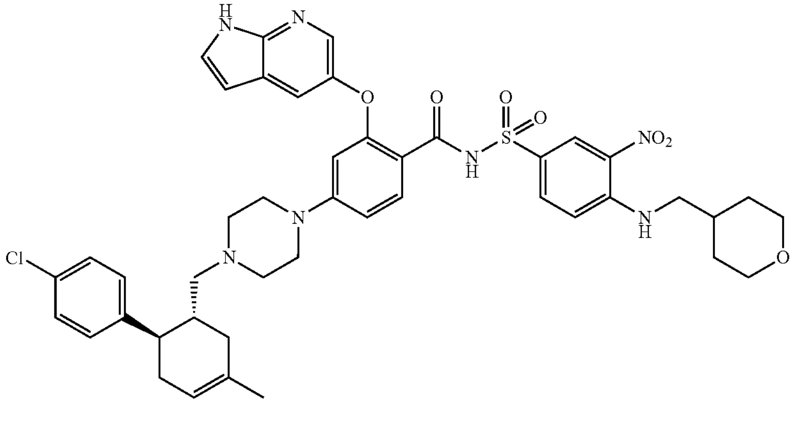 [SMILES: CC1=CC[C@@H](c2ccc(Cl)cc2)[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)C1] | 4-[4-[[(1R,6R)-6-(4-chlorophenyl)-3-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 67 | 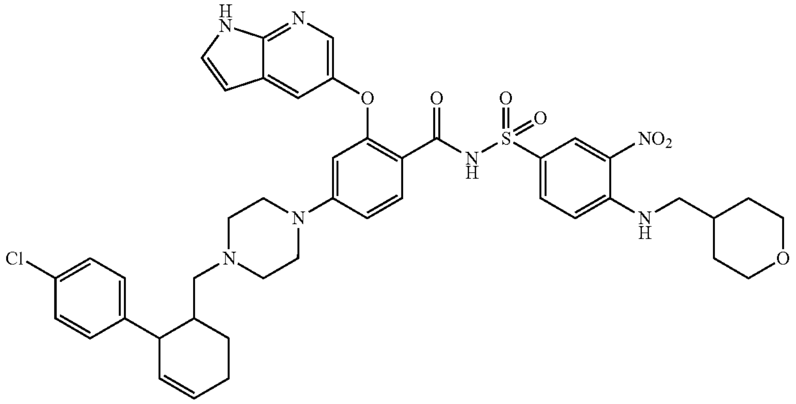 [SMILES: O=C(NS(=O)(=O)c1ccc(NCC2CCOCC2)c([N+](=O)[O-])c1)c1ccc(N2CCN(CC3CCC=CC3c3ccc(Cl)cc3)CC2)cc1Oc1cnc2[nH]ccc2c1] | 4-[4-[[2-(4-chlorophenyl)cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 71 | 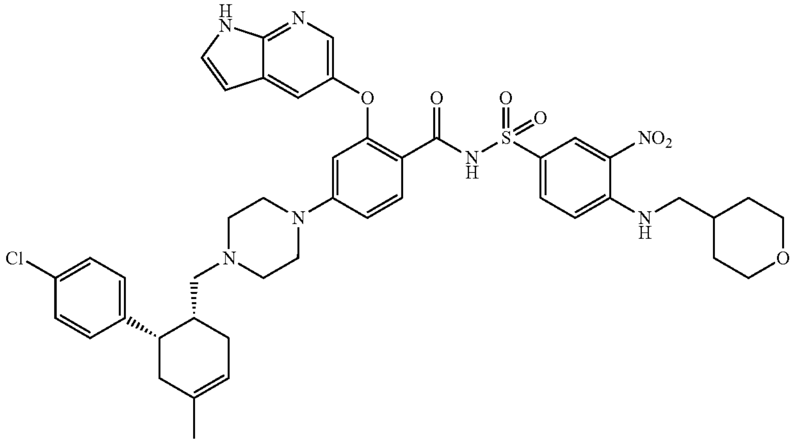 [SMILES: CC1=CC[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)C1] | 4-[4-[[(1R,6S)-6-(4-chlorophenyl)-4-methyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

-continued

| Compound No | Structure | Name |
| --- | --- | --- |
| 74 | 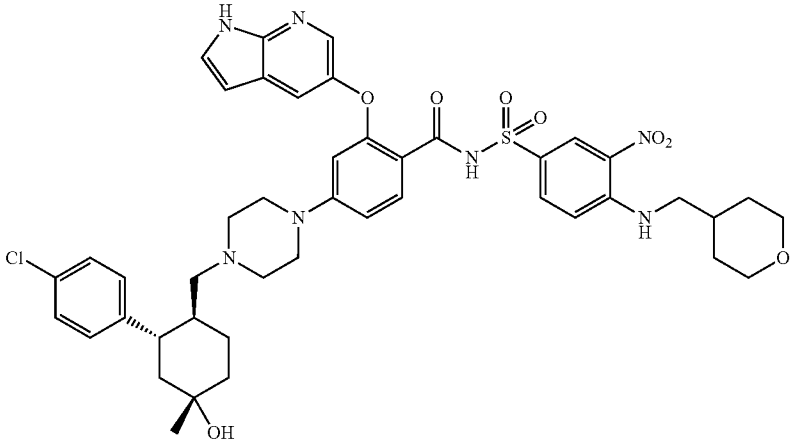 [SMILES: C[C@]1(O)CC[C@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)[C@@H](c2ccc(Cl)cc2)C1] | 4-[4-[[(1S,2S,4S)-2-(4-chlorophenyl)-4-hydroxy-4-methyl-cyclohexyl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |
| 75 | 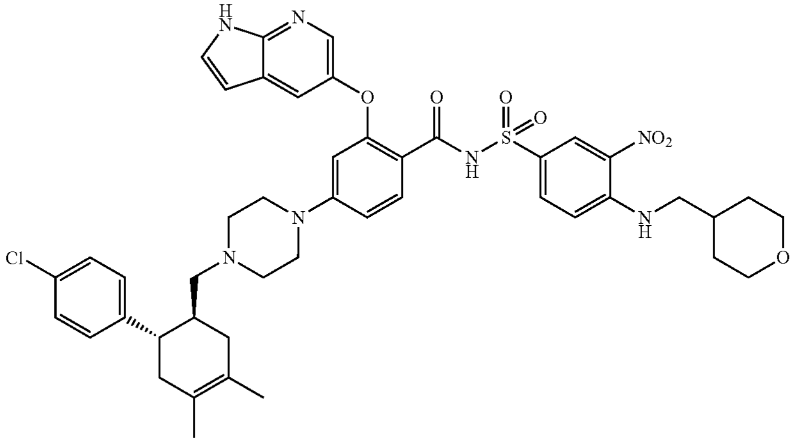 [SMILES: CC1=C(C)C[C@H](c2ccc(Cl)cc2)[C@@H](CN2CCN(c3ccc(C(=O)NS(=O)(=O)c4ccc(NCC5CCOCC5)c([N+](=O)[O-])c4)c(Oc4cnc5[nH]ccc5c4)c3)CC2)C1] | 4-[4-[[(1S,6S)-6-(4-chlorophenyl)-3,4-dimethyl-cyclohex-3-en-1-yl]methyl]piperazin-1-yl]-N-[3-nitro-4-(tetrahydropyran-4-ylmethylamino)phenyl]sulfonyl-2-(1H-pyrrolo[2,3-b]pyridin-5-yloxy)benzamide |

or a pharmaceutically acceptable salt, solvate, or tautomer thereof.

4. A pharmaceutical composition comprising:

a compound of claim 1, or a pharmaceutically acceptable salt, solvate, hydrate, stereoisomer or tautomer thereof; and a pharmaceutically acceptable carrier.

5. The pharmaceutical composition of claim 4, further comprising an additional pharmaceutically active agent.

6. A pharmaceutical composition comprising:

a compound of claim 3, or a pharmaceutically acceptable salt, solvate, hydrate, stereoisomer or tautomer thereof; and a pharmaceutically acceptable carrier.

7. The pharmaceutical composition of claim 6, further comprising an additional pharmaceutically active agent.

8. A method of inhibiting BCL-2, comprising administering to a subject in need of a treatment for cancer a compound of claim 1, or a pharmaceutically acceptable salt, solvate, hydrate, stereoisomer or tautomer thereof.

9. The method of claim 8, wherein the BCL-2 protein is Isoform 1 or Isoform 2.

10. A method of treating a disease or disorder associated with the inhibition of BCL-2, comprising administering to a subject in need of a treatment for cancer a compound of claim 1, or a pharmaceutically acceptable salt, solvate, hydrate, stereoisomer or tautomer thereof.

11. The method of claim 10, wherein the BCL-2 protein is Isoform 1 or Isoform 2.

12. A method of treating cancer, comprising administering to a subject in need of a treatment for cancer a compound of claim 1, or a pharmaceutically acceptable salt, solvate, hydrate, stereoisomer or tautomer thereof.

13. The method of claim 12, wherein the cancer is selected from bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, prostate cancer, marginal zone lymphoma (MZL), follicular lymphoma (FL), diffuse large B-cell lymphoma (DLBCL) and chronic lymphocytic leukemia/small lymphocytic lymphoma (CLL/SLL).

* * * * *